United States Patent
Schmidt (10) Patent No.: US 9,664,320 B2
(45) Date of Patent: May 30, 2017

(54) COUPLING DEVICE FOR THE CONNECTION OF HOSES, ESPECIALLY DENTAL SUPPLY HOSES

(71) Applicant: MEDTRONIC medizinisch-elektronische Gerategesellschaft mbH, Usingen (DE)

(72) Inventor: Alfred Schmidt, Usingen (DE)

(73) Assignee: MEDTRONIC MEDIZINISCH-ELEKTRONISCHE GERAETE-GESELLSCHAFT MIT BESCHRAENKTER HAFTUNG, Weilrod (DE)

( * ) Notice: Subject to any disclaimer, the term of this patent is extended or adjusted under 35 U.S.C. 154(b) by 321 days.

(21) Appl. No.: 14/282,438

(22) Filed: May 20, 2014

(65) Prior Publication Data
US 2014/0353966 A1    Dec. 4, 2014

(51) Int. Cl.
*F16L 33/32* (2006.01)
*A61M 39/10* (2006.01)

(52) U.S. Cl.
CPC .......... *F16L 33/32* (2013.01); *A61M 39/1011* (2013.01); *A61M 2039/1016* (2013.01); *A61M 2039/1027* (2013.01); *A61M 2039/1044* (2013.01)

(58) Field of Classification Search
CPC ..... F16L 37/08; F16L 37/084; F16L 37/0848; F16L 37/02; F16L 37/025; F16L 37/04; F16L 47/06; F16L 47/065; F16L 47/08; F16L 33/32; A61M 2039/1027; A61M 2039/1044; A61M 2039/1016
See application file for complete search history.

(56) References Cited

U.S. PATENT DOCUMENTS 3,667,785 A    6/1972  Kapeker
3,990,727 A *  11/1976 Gallagher ............ F16L 37/084
                                                   285/148.2
(Continued)

FOREIGN PATENT DOCUMENTS

DE      4322868        1/1992
DE      102009016373   10/2010
(Continued)

*Primary Examiner* — David E Sosnowski
*Assistant Examiner* — James A Linford
(74) *Attorney, Agent, or Firm* — Welsh Flaxman & Gitler LLC (57) ABSTRACT

The invention relates to a coupling device for the connection of hoses, a first male connecting element that can be connected to a first hose section and including a male engaging section and a female connecting element that can be releasably coupled with the male connecting element and including a female engaging section. The male engaging section has at least one annular rib with a convex contact surface and the female engaging section has at least one dome section. In the coupled state, the at least one annular rib is engaged from behind by the convex section, in which the dome section, while forming a holding connection, bears against the convex contact surface of the annular rib. As a result of tilting or pivoting of the connecting elements relative to each other the coupled state is releasable by gliding of the convex contact surface from the dome section.

7 Claims, 5 Drawing Sheets

(56) References Cited

U.S. PATENT DOCUMENTS

| | | | | |
|---|---|---|---|---|
| 4,030,850 | A | * | 6/1977 | Hyde ................... B65D 90/08 |
| | | | | 220/795 |
| 5,549,583 | A | * | 8/1996 | Sanford ................ A61M 39/10 |
| | | | | 285/328 |
| 5,797,627 | A | * | 8/1998 | Salter ................... F16L 31/00 |
| | | | | 285/239 |
| 6,059,325 | A | | 5/2000 | Heckele et al. |
| 6,854,771 | B1 | * | 2/2005 | Olson ................... F16L 37/088 |
| | | | | 251/145 |
| 7,811,278 | B2 | * | 10/2010 | Knipple, Jr. ....... A61M 16/0816 |
| | | | | 604/533 |
| 2005/0046185 | A1 | * | 3/2005 | Olson ................... F16L 37/088 |
| | | | | 285/321 |
| 2008/0191466 | A1 | * | 8/2008 | Knipple ............ A61M 16/0816 |
| | | | | 285/31 |
| 2013/0158343 | A1 | | 6/2013 | Honaryar et al. |
| 2013/0164706 | A1 | | 6/2013 | Odabashian et al. |

FOREIGN PATENT DOCUMENTS

| | | |
|---|---|---|
| GB | 2175968 | 12/1986 |
| WO | WO2005030316 | 4/2005 |
| WO | WO 2013/036854 | 3/2013 |
| WO | WO 2013/050319 | 4/2013 |

\* cited by examiner

COUPLING DEVICE FOR THE CONNECTION OF HOSES, ESPECIALLY DENTAL SUPPLY HOSES

BACKGROUND OF THE INVENTION

The invention relates to a coupling device for the connection of hoses, especially for the connection of dental supply hoses.

For the operation of dental instruments, especially electrically and/or pneumatically operated dental instruments, it is necessary to connect the instruments to supply and/or control units. The connection of the instruments to the supply and control units is achieved by means of dental supply hoses. For this purpose, there are coupling devices that can connect both the respective dental instrument to the supply hose and also the supply hose to a supply and control unit.

A dental instrument normally includes a handpiece element and a treatment implement held therein, in the form of a drill or similar implement. A tartar remover preferably implemented using ultrasonic technology or a rinsing unit is also understood to be a dental instrument. The dental instruments comprise in their respective handpiece element electrically or pneumatically operated motor units or ultrasonic units, which are supplied by the supply hose by the supply and control unit with the fluids, electrical power and/or electrical control signals which are required for operation.

In the supply and control of dental instruments, a connection between two supply hoses or between hose sections can also be necessary. The connection of two supply hoses or hose sections is frequently achieved by coupling devices that enable coupling by means of balls or threads or socalled Luer Lock connectors. In such coupling devices, however, the coupled state can be established or released only if the coupling device is easily accessible and can be encompassed by the fingers. Twisting one coupling element off of the other also results in turning or twisting of the hose sections that are connected to the coupling elements, which in many cases is very disadvantageous. German Patent No. DE 196 37 266 C1 describes a coupling for connecting a hose to a medical instrument or to another hose, and in coupled state, a first coupling element having a convex ball surface bears against a concave ball surface of a second coupling element, in which both coupling elements are axially braced against each other in a sealing manner. For this purpose, the first coupling element can be swiveled into a holder located on the second coupling element and for releasing the coupled state can be swiveled out again. Although establishing and releasing the coupled state of the coupling, disclosed in German Patent No. DE 196 37 266 C1, requires no twisting of the first coupling element from the second and eliminates the afore-mentioned disadvantages, the swiveling of the first coupling element into and out of the second coupling element is possible in only one direction, since the holder located on the second coupling element constitutes a rigid limitation or a stop.

It is an object of the invention therefore is to provide a coupling device for the connection of hoses, especially dental supply hoses, which makes it possible to establish and release a coupled state in an especially simple manner that is also gentle on the hoses or supply hoses, especially in tight spatial conditions.

SUMMARY OF THE INVENTION

The invention relates to a coupling device for the connection of hoses, especially for the connection of dental supply hoses. The connection includes at least one first male connecting element that can be connected to a first hose section and comprises a male engaging section and at least one female connecting element that can be releasably coupled with the male connecting element and comprises a female engaging section. It is an essential aspect of the present invention is that the male engaging section comprises at least one annular rib with a convex contact surface and the female engaging section comprises at least one dome section. In the coupled state, the annular rib is engaged from behind by the dome section of the female engaging section and the dome section while forming a holding connection which bears against the convex contact surface of the annular rib of the male engaging section. As a result of tilting or pivoting of the male connecting element relative to the female connecting element, the coupled state is releasable by gliding of the convex contact surface of the annular rib from the dome section.

The female and male connecting elements of the coupling device, according to the invention, for the connection of hoses, especially for the connection of dental supply hoses, respectively comprise a longitudinal axis and an essentially circular cross section, as well as a central through-bore. In the coupled state, the connecting elements are arranged so that the longitudinal axes of the two connecting elements coincide in a common main axis and the through-bores are in alignment with each other. This reliably ensures that the transport or flow of fluids can take place unhindered through the coupling device. In a preferred embodiment, a valve can also be integrated in the coupling device for the directed and controlled flow of fluids.

The coupling device, according to the invention, which can also be referred to as a mini quick coupling, has small outer dimensions, and is therefore suitable for use in tight spatial conditions.

It is especially advantageous that the coupling device, according to the invention, can be used to connect or couple a first hose section with a second hose section. In this respect, the first hose section is connected to the male connecting element of the coupling device and the second hose section is connected with the female connecting element of the coupling device. The coupled state can be achieved by simply plugging the two elements together in coaxial alignment. In this coupled state, the female and male engaging section engage with other in such a manner that the dome section of the female connecting element engages behind the annular ring of the male connecting element. A holding connection between the two connecting elements is established in that the dome section in the female engaging section bears against the convex contact surface of the annular rib in the male engaging section. The axial force of the holding connection in the coupled state is exerted evenly distributed over the circumference of the connecting elements, so that in the coupled state sufficient and reliable retention is ensured in the coaxial alignment of the connecting elements.

It is especially advantageous that the coupled state of the coupling device can be released in a fast and simple manner by tilting or pivoting the two connecting elements in relation to each other. Tilting causes the axial application of force to no longer be evenly distributed over the entire circumference of the connecting elements. At the position at which the axial tension force is greatest, as a result of the convex design of the dome section and the convex contact surface in the coupling device, according to the invention, the dome section glides off of the convex contact surface of the annular rib. The coupled state is released and the connecting elements and therefore the hose sections are then disconnected.

The coupling device according to the invention brings very special advantages, since tilting or pivoting of the connecting elements in relation to each other requires no pre-defined pivoting or tilting direction; instead, the pivoting motion is possible in any direction. In addition, in the coupling device, according to the invention, a small swiveling motion is sufficient for releasing the coupled state, which means that the two connecting elements only have to be brought into a position relative to each other in which the two longitudinal axes enclose an obtuse angle that is only slightly less than 180°. This is especially in view of the fact that connections between supply hoses or hose sections have to be released in very tight spatial conditions, namely within a housing of a supply unit.

Preferably, the female engaging section comprises a conical opening section adjoining an engaging opening and a first cylindrical annular section adjoining the conical opening section. Also, the dome section is located between the first cylindrical annular section adjoining the conical opening section and a second cylindrical annular section. The conical opening section, which reduces the free opening width starting from the first engaging opening to the first cylindrical annular section, facilitates insertion of the male connecting element. The free opening width and therefore the inner diameter of the first cylindrical annular section is expanded by means of the dome section in the direction of the second cylindrical annular section, so that the second cylindrical annular section has a larger inner diameter than the first cylindrical annular section. Due to the location of the dome section between the first and second cylindrical annular section there is a convexly curved transition between the cylindrical annular sections, making it possible to avoid an angular gradation.

The location of the dome section between the first and second cylindrical annular section causes, in the coupled state, engagement of the annular rib behind the male connecting element by the first cylindrical annular section. This engagement of the annular rib can also be understood as a type of locking into place of the first cylindrical annular section behind the annular rib. The engagement or locking into place is achieved due to the reduced inner diameter of the first cylindrical annular section compared with the outer diameter of the annular rib. The second cylindrical annular section, having an inner diameter that corresponds approximately to the outer diameter of the annular rib measured at the summit of the annular rib, bears against the summit of the annular rib in coupled state. The mutual engagement described above and/or the contact or bearing of the aforementioned sections of the male and female engaging sections creates a sealing connection between the two connecting elements.

According to a preferred embodiment of the present invention, the female engaging section additionally comprises a cylindrical base section, in which case, the cylindrical base section while forming a shoulder adjoins the second cylindrical annular section. The inner diameter of the cylindrical base section in this case is greater than that of the second cylindrical annular section. Special advantages result from the fact that the male engaging section comprises a rounded nipple end section and that the annular rib comprises on the side facing the nipple end section an insertion curvature for easier gliding insertion into the female engaging section. The insertion curvature of the annular rib lies opposite the convex contact surface and preferably has a radius of curvature in a range between 4 mm and 6 mm. It is especially preferred that the convex contact surface of the annular rib has a radius of curvature in a range between 2 mm and 4 mm.

Advantageously, the male connecting element, in the area of the male engaging section, additionally comprises a circumferential annular groove for accommodating a sealing element, in which case the annular groove on the side facing away from the nipple end section adjoins the annular rib. The coupling device can be additionally sealed by a sealing element inserted into the annular groove, thus ensuring for the supply hoses to be connected that no leaks occur within the coupling device during the transport of fluids. Sealing rings made of rubber or plastic, especially O-rings, can be used as sealing elements.

Preferably the dome section of the female engaging section has a convex curvature with a radius of curvature in a range between 1 mm and 3 mm.

According to an especially preferred embodiment of the present invention, straight hose connectors are provided for connection of the male connecting element to a first hose section and for connection of the female connecting element to a second hose section. The hose connectors can be manufactured from plastic or metal, and especially from brass.

The male and female connecting elements are preferably manufactured from a plastic material, especially a thermoplastic material, for example polypropylene.

The invention is described below in more detail based on exemplary embodiments with reference to the drawings. Further embodiments, advantages and applications of the invention are also disclosed in the following description of the exemplary embodiments and the drawings.

BRIEF DESCRIPTION OF THE DRAWINGS

The invention is illustrated in the following drawings, where.

DETAILED DESCRIPTION OF THE INVENTION

Figure 1:
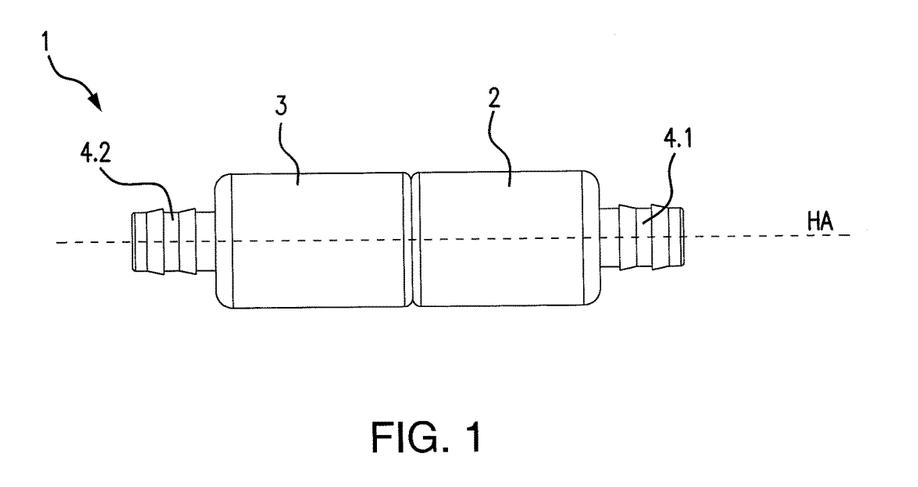
FIG. 1 schematically depicts a coupling device according to the present invention in side view.

FIG. 1 shows a side view of a coupling device 1 according to the invention for the connection of hoses, especially for the connection of dental supply hoses, in coupled state.

The coupling device 1 includes a male connecting element 2 that can be connected to a first hose section (not shown) and a female connecting element 3 that can be connected to a second hose section (not shown) and releasably connected to the male connecting element 2. In the depicted example, two straight hose connectors 4.1, 4.2 are provided for connection of the hose sections to the two connecting elements 2, 3. The hose connectors 4.1, 4.2 are, for example, simple plug-type connectors, which are inserted at the ends of the male and female connecting elements 2, 3 facing away from the coupling sides and are for the mounting of hose sections.

The female and male connecting elements 2, 3 of the coupling device 1 according to the invention for the connection of hoses, especially for the connection of dental supply hoses, have an essentially circular cross section with a respective outer diameter in a range between 6 mm and 7 mm. In the coupled state, the connecting elements 2, 3 are arranged so that longitudinal axes LA1, LA2 (not depicted in FIG. 1; see FIGS. 2 and 3) of the two connecting elements 2, 3 coincide in a common main axis HA (see FIG. 4). The two connecting elements 2, 3 and the hose connectors 4.1, 4.2 are arranged coaxially in the coupled state depicted in FIG. 1.

Figure 2:
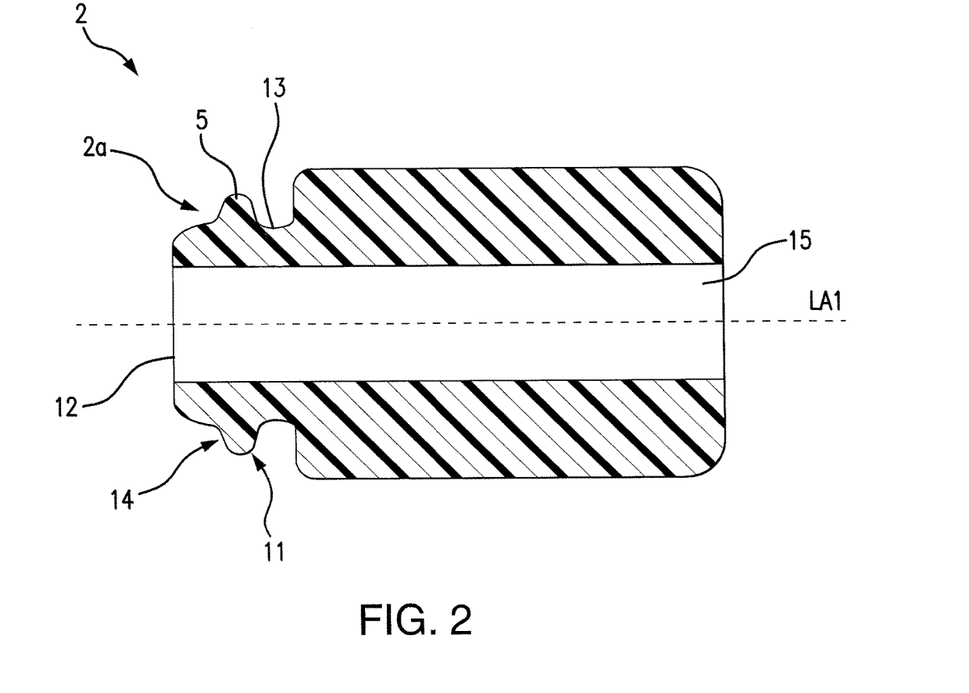
FIG. 2 shows a longitudinal cross section of a male connecting element.
Figure 3:
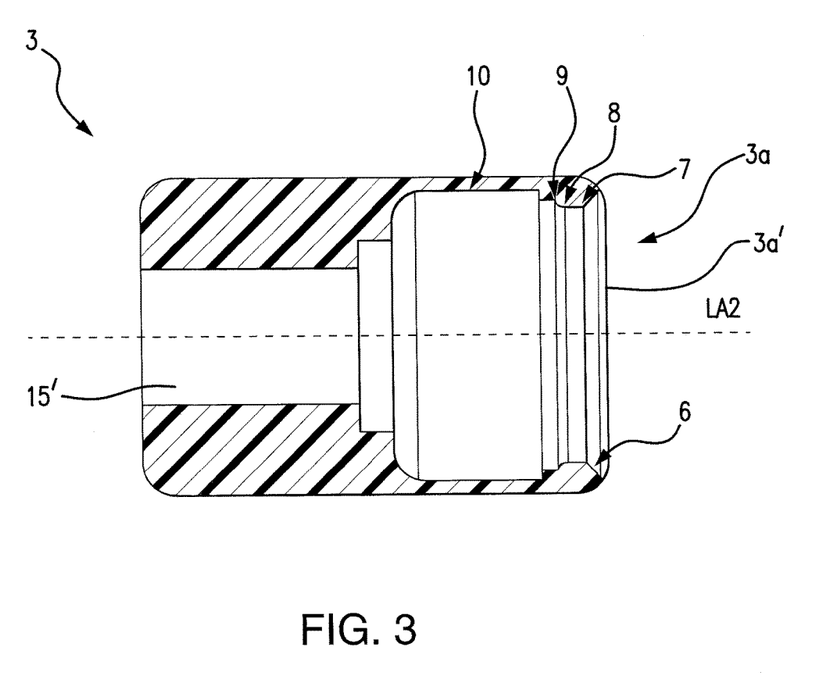
FIG. 3 shows a longitudinal cross section of a female connecting element.

FIGS. 2 and 3 respectively show the male connecting element 2 and the female connecting element 3 in longitudinal cross section. The male connecting element 2 depicted in FIG. 2 comprises a central through-bore 15 extending along the longitudinal axis LA1 for the fluid transport and a male engaging section 2a for engaging in the female connecting element 3. The male engaging section 2a comprising a rounded nipple end section 12 lies in an axial direction opposite the end of the male connecting element 2 that can be connected to a hose section. According to the invention the male connecting element 2 comprises an annular rib 5 in the area of the male engaging section 2a. The circumferentially designed annular rib 5 adjoins the nipple end section 12 in an axial direction and provides on the side facing the nipple end section 12 an insertion curvature 14 for easier insertion or pushing into the female connecting element 3. The circumferential annular rib 5 comprises on the side opposite the insertion curvature 14 a convex contact surface 11, the convex contact surface 11 being designed to provide contact to the female connecting element 3 as a holding contact in the coupled state that however is releasable.

The outer diameter of the annular rib 5 measured at the summit of the annular rib 5 is about 1.2 times to 1.4 times greater than the outer diameter of the nipple end section 12, which is in a range between about 4 mm and 4.5 mm.

Figure 4:
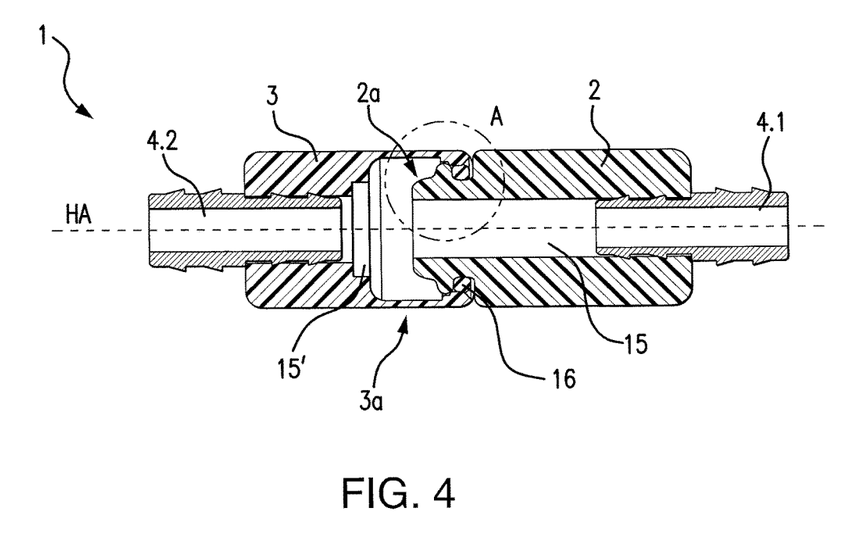
FIG. 4 schematically depicts a longitudinal cross section through the coupling device of FIG. 1.
Figure 5:
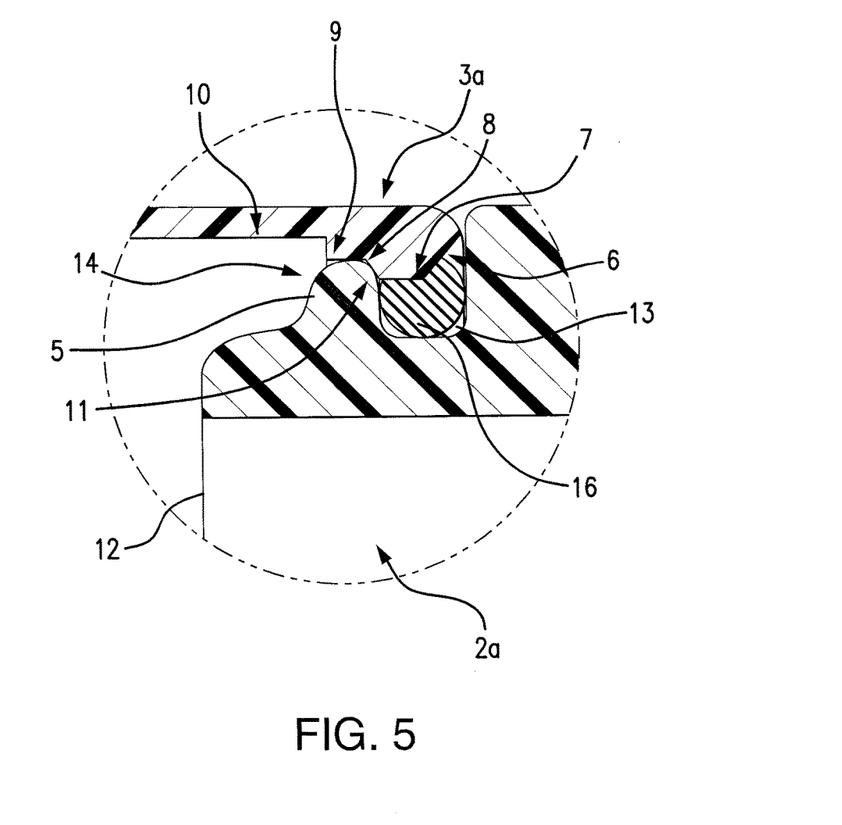
FIG. 5 shows the cutout A of FIG. 4 in an enlarged view.

In the depicted example, the annular rib 5 adjoins on the side facing away from the nipple end section 12 a circumferential annular groove 13 for accommodating a sealing element 16 (not depicted in FIG. 2; see FIGS. 4 and 5).

The female connecting element 3 depicted in FIG. 3 likewise comprises a central through-bore 15' extending along a longitudinal axis LA2 and a female engaging section 3a for engaging in the male connecting element 2. The female engaging section 3a comprising an engaging opening 3a' lies in axial direction opposite the end of the female connecting element 3 that can be connected to a hose section. The engaging opening 3a' has a free opening width in a range between 5 mm and 5.8 mm. According to the invention, the female connecting element 3 comprises in the area of the female engaging section 3a at least one dome section 8, which in the coupled state, while forming a holding connection, bears against the convex contact surface 11 of the annular rib 5 of the male connecting element 2.

In the depicted example, the dome section 8 is located between a first cylindrical annular section 7 and a second cylindrical annular section 9, and the inner diameter of the first cylindrical annular section 7, at about 4.9 mm to 5.3 mm, is smaller than the inner diameter of the second cylindrical annular section 9. Toward the engaging opening 3a', adjoining the first cylindrical annular section 7, is a conical opening section 6, which ensures facilitated insertion of the male connecting element 2 into the female connecting element 3. On the side facing away from the engaging opening 3a', adjoining the second cylindrical annular section 9, is a cylindrical base section 10, in which in the coupled state the nipple end section 12 of the male connecting element 2 is accommodated. Starting from the engaging opening 3a' of the female engaging section 3a, adjoining each other in axial direction successively are the conical opening section 6, the first cylindrical annular section 7, the dome section 8, the second cylindrical annular section 9 and the cylindrical base section 10. This succession of the sections of the female engaging section 3a in combination with the embodiment of the male engaging section 2a described above enables both easy connection and also easy disconnection of the male and female connecting elements 2, 3.

FIG. 4 shows schematically a longitudinal cross section through the coupling device 1 in the coupled state. The male engaging section 2a of the male connecting element 2 is accommodated in the coupled state by the female engaging section 3a of the female connecting element 3. The male and female connecting elements 2, 3 are therefore arranged coaxially along the common main axis HA, through which the central through-bores 15, 15' are in alignment with each other and provide an unhindered passageway for the transport and/or flow of fluids. In the coupled state a holding connection between the two connecting elements 2, 3 is established by the fact that the dome section 8 of the female connecting element 3 adjoins the convex contact surface 11 of the male connecting element (see FIG. 5), by which the axial force of the holding connection in the coupled state is applied evenly distributed over the circumference of the two connecting elements 2, 3. In the coupled state, sufficient and reliable retention is ensured in the coaxial alignment of the connecting elements 2, 3.

FIG. 5 shows the enlarged cutout A of FIG. 4, depicting a cutout of the male and female engaging sections 2a, 3a in the coupled state. The holding connection between the two connecting elements 2, 3 is established in the coupled state by the fact that the dome section 8 of the female engaging section 3a bears against the convex contact surface 11 of the annular rib 5 of the male engaging section 2a and simultaneously the first cylindrical annular section 7 engages behind the annular rib 5 on the side facing away from the nipple end section 12. The engaging of the annular rib 5 by the first cylindrical annular section 7 can also be understood as a type of locking into place of the first cylindrical annular section 7 behind the annular rib 5. The engaging or locking into place is achieved due to the reduced inner diameter of the first cylindrical annular section 7 compared with the outer diameter of the annular rib 5. The second cylindrical annular section 9, having an inner diameter that corresponds approximately to the outer diameter of the annular rib 5 measured at the summit of the annular rib 5, bears against the summit of the annular rib 5. The mutual engaging of the male connecting sections 2a, 3a described above, namely by the dome section 8 bearing against the convex contact surface 11 of the annular rib 5 and the bearing of the second cylindrical annular section 9 on the summit of the annular rib 5 establishes a sealing connection by means of the coupling device. To support the sealing of the sealing connection the male engaging section 2a in the depicted example additionally comprises an annular groove 13, in which a sealing element 16 is accommodated.

To release the coupled state and/or to disconnect the male and female connecting elements 2, 3 it is only necessary to tilt or pivot the two connecting elements 2, 3. Tilting or pivoting the male connecting element 2 in relation to the female connecting element 3 means that the axial force is no longer applied evenly distributed over the entire circumference of the two connecting elements 2, 3. At the location at which the axial tension force occurring is greatest due to tilting, in the coupling device 1 according to the invention, the result is a gliding of the convex dome section 8 from the convex contact surface 11 of the annular rib 5 and the coupled state is released. In the depicted example, the convex contact surface 11 of the annular rib 5 has a radius of curvature in a range between 2 mm and 4 mm and the convex dome section 8 in the female connecting element 3 has a radius of curvature in a range between 1 mm and 3 mm.

The invention was described above based on an exemplary embodiment. It goes without saying that numerous variations and modifications of the invention are possible without abandoning the underlying inventive concept.

REFERENCE LIST

1 coupling device
2 male connecting element
2a male engaging section
3 female connecting element
3a female engaging section
3a' engaging opening
4.1, 4.2 hose connector
5 annular rib
6 conical opening section
7 first cylindrical annular section
8 dome section
9 second cylindrical annular section
10 cylindrical base section
11 convex contact surface
12 nipple end section
13 annular groove
14 insertion curvature
15, 15' central through-bore
16 sealing element0
LA1 longitudinal axis
LA2 longitudinal axis
HA main axis

What is claimed is:

1. A bend coupling device for a connection of hoses, the bend coupling device comprising:
    a male connecting element that is connectable to a first hose section, the male connecting element comprising a male engaging section; and
    a female connecting element releasably coupled with the male connecting element, the female connecting element comprising a female engaging section;
    the male engaging section further comprises an annular rib with a convex contact surface having a curvature and the female engaging section further comprises a dome section, in which in a state, a longitudinal axis (LA1) of the male connecting element and a longitudinal axis (LA2) of the female connecting element are arranged coaxially and form a common main axis (HA) of the bend coupling device and the dome section of the female engaging section engages behind the annular rib of the male engaging section and while forming a holding connection, the dome section bears against the convex contact surface of the annular rib, the male connecting element in an area of the male engaging section further comprises a rounded nipple end section and a circumferential annular groove for accommodating a sealing element, the circumferential annular groove on a side facing away from the nipple end section adjoins the annular rib and a sealing element is inserted into the annular groove and in which, release of the male connecting element from the female connecting element from the coupled state results from tilting or pivoting the male connecting element and the female connecting element in relation to each other by bringing the male connecting element and the female connecting element into a position relative to each other in which the longitudinal axis (LA1) of the male connecting element and the longitudinal axis (LA2) of the female connecting element are angled obtusely less than 180°, and whereby the coupled state is released by gliding of the convex contact surface of the annular rib from the dome section, wherein the female engaging section further comprises a conical opening section adjoining an engaging opening and a first cylindrical annular section adjoining the conical opening section, and the dome section is located between the first cylindrical annular section adjoining the conical opening section and a second cylindrical annular section, and wherein the conical opening section and the first cylindrical annular section are both at least partly contained in the groove and the conical opening section and the first cylindrical annular section both abut the seal.

2. The bend coupling device according to claim 1, wherein the female engaging section further comprises a cylindrical base section, the cylindrical base section while forming a shoulder adjoins the second cylindrical annular section.

3. The bend coupling device according to claim 1, wherein the annular rib comprises on a side facing of a nipple end section, an insertion curvature for gliding insertion into the female engaging section, the insertion curvature lies opposite the convex contact surface of the annular rib and has a radius of curvature in a range between 4 mm and 6 mm.

4. The bend coupling device according to claim 1, the convex contact surface of the annular rib has a radius of curvature in a range between 2 mm and 4 mm.

5. The bend coupling device according to claim 1, wherein the dome section of the female engaging section has a convex curvature with a radius of curvature in a range between 1 mm and 3 mm.

6. The bend coupling device according to claim 1, wherein two straight hose connectors are provided for connection of the male connecting element to a first hose section and for connection of the female connecting element to a second hose section.

7. The bend coupling device according to claim 1, wherein the male connecting element and the female connecting element are a plastic material, a thermoplastic material, or a polypropylene.

* * * * *

UNITED STATES PATENT AND TRADEMARK OFFICE
CERTIFICATE OF CORRECTION

PATENT NO. : 9,664,320 B2
APPLICATION NO. : 14/282438
DATED : May 30, 2017
INVENTOR(S) : Alfred Schmidt It is certified that error appears in the above-identified patent and that said Letters Patent is hereby corrected as shown below:

Column 7, Line 40 through Column 8, Line 30, cancel the text beginning with "1. A bend coupling" to and ending "abut the seal", and insert the following claim:

--1. A bend coupling device for a connection of hoses, the bend coupling device comprising: a male connecting element that is connectable to a first hose section, the male connecting element comprising a male engaging section; and a female connecting element releasably coupled with the male connecting element, the female connecting element comprising a female engaging section; the male engaging section further comprises an annular rib with a convex contact surface having a curvature and the female engaging section further comprises a dome section, in which in a coupled state, a longitudinal axis (LA1) of the male connecting element and a longitudinal axis (LA2) of the female connecting element are arranged coaxially and form a common main axis (HA) of the bend coupling device and the dome section of the female engaging section engages behind the annular rib of the male engaging section and while forming a holding connection, the dome section bears against the convex contact surface of the annular rib, the male connecting element in an area of the male engaging section further comprises a rounded nipple end section and a circumferential annular groove for accommodating a sealing element, the circumferential annular groove on a side facing away from the nipple end section adjoins the annular rib and a sealing element is inserted into the annular groove and in which, release of the male connecting element from the female connecting element from the coupled state results from tilting or pivoting the male connecting element and the female connecting element in relation to each other by bringing the male connecting element and the female connecting element into a position relative to each other in which the longitudinal axis (LA1) of the male connecting element and the longitudinal axis (LA2) of the female connecting element are angled obtusely less than 180°, and whereby the coupled state is released by gliding of the convex contact surface of the annular rib from the dome section, wherein the female engaging section further comprises a conical opening section adjoining an engaging opening and a first cylindrical annular section adjoining the conical opening section, and the dome section is located between the first Signed and Sealed this
Eighteenth Day of July, 2017

Joseph Matal
*Performing the Functions and Duties of the*
*Under Secretary of Commerce for Intellectual Property and*
*Director of the United States Patent and Trademark Office* cylindrical annular section adjoining the conical opening section and a second cylindrical annular section, and wherein the conical opening section and the first cylindrical annular section are both at least partly contained in the groove and the conical opening section and the first cylindrical annular section both abut the seal.--